US00PP23751P2

(12) United States Plant Patent
Smith

(10) Patent No.: US PP23,751 P2
(45) Date of Patent: Jul. 16, 2013

(54) ***CHRYSANTHEMUM* PLANT NAMED 'CIFZ0030'**

(50) Latin Name: *Chrysanthemum×morifolium*
Varietal Denomination: CIFZ0030

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 34 days.

(21) Appl. No.: 13/385,182

(22) Filed: Feb. 6, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — Joshua L. Price

(57) ABSTRACT

A new *Chrysanthemum* plant named 'CIFZ0030' particularly distinguished by the medium sized yellow inflorescences, medium green foliage, nice round plant habit with good stem strength and a natural season flowering response of mid-September.

1 Drawing Sheet

Latin name of the genus and species of the plant claimed: *Chrysanthemum×morifolium.*

Varietal denomination: 'CIFZ0030'.

BACKGROUND OF THE NEW PLANT

The present invention comprises a new *Chrysanthemum*, botanically known as *Chrysanthemum×morifolium*, and hereinafter referred to by the variety name 'CIFZ0030'.

'CIFZ0030' is a product of a planned breeding program. The new cultivar has medium sized yellow inflorescences, medium green foliage, nice round plant habit with good stem strength and a natural season flowering response of mid September.

'CIFZ0030' originated from a hybridization made in a greenhouse in December 2007 in a controlled breeding environment in a greenhouse in Amanecer, Columbia. The female parent was the proprietary plant designated 'Yoelena', U.S. Plant Pat. No. 20,212, with larger inflorescences with a darker shade of yellow and a black cloth flowering response a half a week slower and a smaller plant habit than 'CIFZ0030'.

The male parent of 'CIFZ0030' was a proprietary plant identified as 'Yodiana', U.S. Plant Pat. No. 17,535, with more disk florets, weaker stems with more plant splitting, more upright plant habit than that of 'CIFZ0030'. The resultant seed was sown and grown outdoors in June 2008 in Alva, Fla.

'CIFZ0030' was selected as one flowering plant within the progeny of the stated cross in October 2008 in Alva, Fla.

The first act of asexual reproduction of 'CIFZ0030' was accomplished when vegetative cuttings were propagated from the initial selection in December 2008 in a greenhouse in Alva, Fla.

BRIEF SUMMARY OF INVENTION

Horticultural examination of plants grown from cuttings of the plant initiated in December 2008, and continuing thereafter, has demonstrated that the combination of characteristics as herein disclosed for 'CIFZ0030' are firmly fixed and are retained through successive generations of asexual reproduction.

'CIFZ0030' has not been observed under all possible environmental conditions. The phenotype may vary significantly with variations in environment such as temperature, light intensity and day length.

A Plant Breeder's Right for this cultivar was applied for in Canada on Feb. 24, 2011, No. 11-7187. 'CIFZ0030' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0030' with colors being as true as possible with an illustration of this type. The photographic drawing shows a flowering plant of the new variety, and a close-up of the inflorescences.

DETAILED BOTANICAL DESCRIPTION

The plant descriptions, measurements and aforementioned photographs were taken outdoors in Gilroy, Calif. in early August 2011. The plants were growing in an outdoor potted plant trial, in one gallon pots, in full sun. These plants were approximately 9-10 weeks of age.

Color references are made to The Royal Horticultural Society Colour Chart (R.H.S.) 2001.

TABLE 1

DIFFERENCES BETWEEN THE NEW VARIETY 'CIFZ0030' AND A MOST SIMILAR VARIETY

| | 'CIFZ0030' | 'Golden Yohelga' (U.S. Plant Pat. No. 15,317) |
|---|---|---|
| Quantity of disc florets: | Fewer | More |
| Stem strength (plant splitting in bad weather): | Stronger (less apt) | Weaker (more apt) |
| Black cloth flowering response: | 10 days faster | Slower |

Plant:

*Form, growth and habit.*—Herbaceous garden-type, stems upright and outwardly spreading, freely branching, strong and moderately vigorous growth habit.

*Plant height.*—20.0-22.0 cm.

*Plant height (inflorescence included).*—24.0-26.0 cm.

*Plant width.*—36.0-40.0 cm.

Roots:

*Number of days to initiate roots.*—About 5 days at about 22 degrees C.

*Number of days to produce a rooted cutting.*—About 7-10 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Closest to RHS 137C.

*Mature, leaf color, upper surface.*—RHS 137A but a little darker.

*Lower surface.*—Closest to RHS 137C.

*Length.*—4.5-4.9 cm.

*Width.*—2.6-4.0 cm.

*Shape.*—Ovate.

*Base shape.*—Attenuate.

*Apex shape.*—Acute to abruptly acute.

*Margin.*—Palmately lobed; irregularly incised; serrate.

*Texture, upper surface.*—Bifid T-shaped hairs.

*Lower surface.*—Bifid T-shaped hairs.

*Color of veins, upper surface.*—Indistinct.

*Color of veins, lower surface.*—Indistinct.

*Petiole color.*—Closest to RHS 138A.

*Length.*—2.0-2.3 cm.

*Diameter.*—0.2 cm.

*Texture.*—Bifid T-shaped hairs.

Stem:

*Quantity of main branches per plant.*—8-9.

*Color of stem.*—Closest to RHS 146A.

*Length of stem.*—10.0-12.0 cm.

*Diameter.*—0.5 cm.

*Length of internodes.*—1.0-1.5 cm.

*Texture.*—Bifid T-shaped hairs.

*Color of peduncle.*—Closest to RHS 146A.

*Length of peduncle.*—6.5-8.5 cm.

*Peduncle diameter.*—0.1-0.15 cm.

*Texture.*—Bifid T-shaped hairs.

Inflorescence:

*Type.*—Compositae, solitary, decorative-type inflorescences, borne terminally above foliage, ray florets arranged acropetally on a capitulum.

*Quantity of inflorescences per plant.*—About 100 with about 100 buds.

*Lastingness of individual blooms on the plant.*—More than 6 weeks from the first Color showing.

*Fragrance.*—Slightly spicy.

Bud (just when opening/showing color):

*Color.*—RHS 5B to RHS 5C.

*Length.*—0.7-1.3 cm.

*Width.*—1.1-1.2 cm.

*Shape.*—Oblate.

Immature inflorescence:

*Diameter.*—4.3-4.7 cm.

*Color of ray florets, upper surface.*—Closest to RHS 5B.

*Lower surface.*—RHS 5C.

Mature inflorescence:

*Diameter.*—5.0-5.4 cm.

*Depth.*—1.5 cm.

*Total diameter of 'disc'.*—Indistinct at this phase.

*Receptacle height.*—0.5 cm.

*Receptacle diameter.*—0.5-0.6 cm.

Ray florets:

*Average quantity of florets.*—Between 125 and 150 in numerous whorls.

*Color of florets, upper surface.*—Closest to RHS 5B with a few specks of RHS 5A towards the apex.

*Lower surface.*—RHS 5C.

*Length.*—2.2-2.3 cm.

*Width.*—0.45-0.5 cm.

*Shape.*—Oblong.

*Apex shape.*—Rounded to slightly and irregularly retuse.

*Margin.*—Entire.

*Texture, upper surface.*—Papillose.

*Lower surface.*—Papillose.

Disc florets:

*Average quantity of florets.*—20-30.

*Color of florets.*—RHS 1C, with RHS 14A to RHS 14B at the apex.

*Length.*—0.45-0.5 cm.

*Width.*—0.1 cm.

*Shape.*—Tubular, elongated.

*Apex shape.*—Acute, 5 pointed.

Phyllaries:

*Quantity.*—20-24.

*Color, upper surface.*—Closest to RHS 137B.

*Lower surface.*—Between RHS 137A and RHS 137B.

*Length.*—0.5-0.6 cm.

*Width.*—0.2 cm.

*Shape.*—Lanceolate.

*Apex shape.*—Acute.

*Base.*—Fused.

*Margins.*—Entire.

*Texture, upper surface.*—Glabrous.

*Lower surface.*—Bifid T-shaped hairs.

Reproductive organs:

*Pistil.*—1, found on both floret types.

*Length.*—0.25-0.3 cm.

*Style color.*—RHS 1C.

*Style length.*—0.15-0.2 cm.

*Stigma color.*—RHS 9B.

*Stigma shape.*—Bi-parted.

*Ovary color.*—RHS 155C.

*Ovary length.*—0.1 cm.

*Ovary width.*—0.05 cm.

*Stamens*.—4, found on only disc florets.

*Color of filaments*.—RHS 1C.

*Length filaments*.—0.4 cm.

*Anther color*.—RHS 13B.

*Anther length*.—0.15 cm.

*Anther shape*.—Oblong.

*Color of pollen*.—RHS 13A.

*Pollen amount*.—Scarce.

What is claimed is:

1. A new and distinct variety of *Chrysanthemum* plant named 'CIFZ0030' substantially as illustrated and described herein.

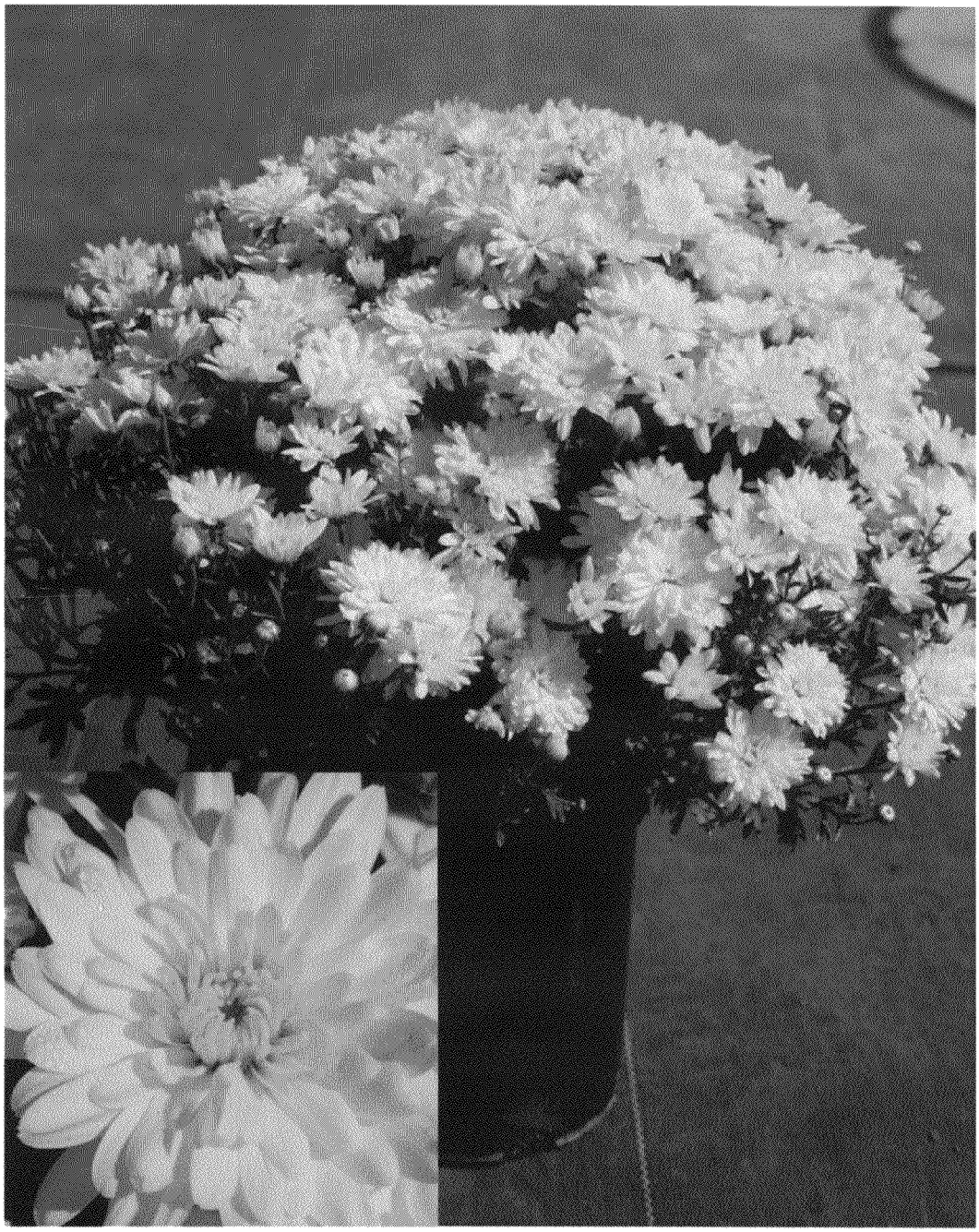

* * * * *